United States Patent
Bishop et al.

(10) Patent No.: US 6,605,450 B1
(45) Date of Patent: Aug. 12, 2003

(54) **IRON REGULATION OF THE PPSEC10 TRANSCRIPTIONAL REGULATORY REGION OF *PICHIA PASTORIS* AND METHODS OF USE**

(75) Inventors: Robert J. Bishop, Berkeley, CA (US); Kenneth A. Crawford, Alameda, CA (US); Margaret M. Worden, Kensington, CA (US)

(73) Assignee: Chiron Corporation, Emeryville, CA (US)

( * ) Notice: Subject to any disclaimer, the term of this patent is extended or adjusted under 35 U.S.C. 154(b) by 0 days.

(21) Appl. No.: 09/866,274

(22) Filed: May 24, 2001

Related U.S. Application Data

(60) Provisional application No. 60/207,009, filed on May 25, 2000.

(51) Int. Cl.[7] .......................... C12P 21/02; C12N 15/11; C12N 15/63; C12N 15/81
(52) U.S. Cl. ................... 435/69.1; 435/320.1; 435/483; 536/24.1
(58) Field of Search ............................ 436/69.1, 320.1, 436/483; 536/24.1

(56) References Cited

U.S. PATENT DOCUMENTS

| | | | |
|---|---|---|---|
| 5,215,898 | A | 6/1993 | Bolen et al. |
| 5,324,639 | A | 6/1994 | Brierley et al. |
| 5,324,660 | A | 6/1994 | Gleeson et al. |
| 5,521,086 | A | 5/1996 | Scott et al. |
| 5,602,034 | A | 2/1997 | Tekamp-Olson |
| 6,410,264 | B1 | 6/2002 | Crawford et al. |

FOREIGN PATENT DOCUMENTS

| | | |
|---|---|---|
| EP | 0 495 208 A2 | 7/1992 |
| WO | WO 94/21802 | 9/1994 |
| WO | WO 96/40776 | 12/1996 |
| WO | WO 97/12044 | 4/1997 |
| WO | WO 99/07862 | * 2/1999 |

OTHER PUBLICATIONS

Buckholz, Richard G., "Yeast Systems for the Expression of Heterologous Gene Products," *Current Opinion in Biotechnology*, 1993, pp. 538–542, vol. 4, Current Biology Ltd.

Busser, K., et al., "Heterologous Protein Expression in *Pichia pastoris*," *American Biotechnology Laboratory*, 1993, pp. 10–EOA, vol. 11(13), International Scientific Communications.

Cregg, James M., et al., "Recent Advances in the Expression of Foreign Genes in *Pichia pastoris*," *Bio/Technology*, Aug. 1993, pp. 905–910, vol. 11.

Payne, William E., et al., "An Inducible Acid Phosphatase from the Yeast *Pichia pastoris*: Characterization of the Gene and Its Product," *Gene*, 1995, pp. 19–26, vol. 163, Elsevier Science B.V.

Romanos, Michael A., et al., "Foreign Gene Expression in Yeast: A Review," *Yeast*, Jun. 1992, pp. 423–488, vol. 8, John Wiley & Sons Ltd.

Sreekrishna, Koti, et al., "Strategies for Optimal Synthesis and Secretion of Heterologous Proteins in the methylotrophic Yeast *Pichia pastoris*," *Gene*, 1997, pp. 55–62, vol. 190, Elsevier Science B.V.

Genbank Database Report for Accession No. U52430, May 28, 1996 (XP–002084510).

* cited by examiner

*Primary Examiner*—Terry McKelvey
(74) *Attorney, Agent, or Firm*—W. Murray Spruill; Joseph H. Guth; Robert P. Blackburn

(57) ABSTRACT

Methods and compositions for the expression of nucleotide sequences are provided. Compositions comprise the nucleic acid sequences of the transcriptional regulatory region of the PpSEC10 gene of *Pichia pastoris*. Methods are provided to chemically regulate the PpSEC10 transcriptional control region by modulating the iron concentration in the culturing medium. The methods find use in regulating expression of nucleotide sequences. Furthermore, the methods of the invention can be used to regulate polypeptide expression, more particularly in regulating heterologous polypeptide expression, particularly using a yeast host cell as the expression system.

54 Claims, No Drawings

IRON REGULATION OF THE PPSEC10 TRANSCRIPTIONAL REGULATORY REGION OF *PICHIA PASTORIS* AND METHODS OF USE

CROSS-REFERENCE TO RELATED APPLICATION

This application claims the benefit of U.S. Provisional Application No. 60/207,009 filed May 25, 2000, which is herein incorporated by reference in its entirety.

FIELD OF THE INVENTION

The present invention relates to the expression of nucleic acid sequences of interest.

BACKGROUND OF THE INVENTION

The PpSEC10 gene of *P. pastoris* encodes a precursor polypeptide that comprises a secretion leader and a polypeptide sequence for the mature form of a 10 kDa yeast-secreted polypeptide designated the SEC10p polypeptide. This precursor polypeptide represents the initial translation product of mRNA transcribed from the PpSEC10 gene. The PpSEC10 precursor polypeptide has some structural components that are typical of secreted polypeptides: a secretion leader with a hydrophobic N-terminal sequence that is characteristic of the secretion signal, a mature polypeptide sequence, and two basic amino acids that are positioned at the C-terminus of the secretion leader and which directly precede the mature polypeptide sequence. Dibasic residues are a common cleavage recognition sequence for processing proteases such as Kex2.

The predicted molecular weight of the mature form of SEC10p based on the amino acid sequence is 10 kDa, while the estimated molecular weight of the secreted polypeptide based on SDS-PAGE mobility is 18 kDa, indicating SEC10p is glycosylated. Wild-type *Pichia pastoris* cells secrete high levels of the mature SEC10p polypeptide following proteolytic processing of the precursor polypeptide to remove the secretion leader that directs movement of the mature SEC10p polypeptide through the secretory pathway of the yeast cell.

The regulatory and coding sequences of the PpSEC10 gene are provided in Publication No. WO 99/24062, entitled "Novel *Pichia pastoris* Gene Sequences and Methods for Their Use," herein incorporated by reference. Nucleotide sequences comprising the PpSEC10 gene were deposited with the American Type Culture Collection, Rockville, Md., on Feb. 5, 1997 (Accession No. 98315) and on Jun. 6, 1997 (Accession No. 98450).

The present invention provides methods and compositions for the regulated expression of nucleic acid sequences using the transcriptional regulatory region of the PpSEC10 gene of *Pichia pastoris*. The methods find use in the expression of nucleotide sequences of interest and in the production of commercially significant concentrations of heterologous polypeptides.

SUMMARY OF THE INVENTION

Methods and compositions are provided for the expression of a nucleotide sequence of interest using regulatory sequences of the PpSEC10 gene of *Pichia pastoris*. Methods comprise means to chemically regulate the PpSEC10 transcriptional control region by modulating iron concentration in the culturing medium. The methods find use in regulating expression of nucleotide sequences. Furthermore, the methods of the invention can be used to regulate polypeptide expression, more particularly in regulating heterologous polypeptide expression, particularly using a yeast host cell as the expression system.

Compositions of the invention include a DNA construct comprising a transcriptional regulatory region, operably linked to a heterologous transcriptional initiation region operably linked to a nucleotide sequence of interest, wherein said transcriptional regulatory region comprises the sequence set forth in SEQ ID NO:1 or a variant or fragment thereof. Compositions of the invention further include an expression vector comprising this DNA construct.

Methods are provided to regulate the expression of a nucleotide sequence of interest comprising stably introducing into the genome of a yeast host cell at least one DNA construct comprising, in proper reading frame, an Fe-responsive PpSEC10 transcriptional regulatory region comprising the nucleotide sequence set forth in SEQ ID NO:1 or a variant or fragment thereof, a heterologous transcriptional initiation region, and a nucleotide sequence encoding said nucleotide sequence of interest, and culturing said yeast cells in media.

Methods of the invention also provide a means to regulate expression of a nucleotide sequence of interest comprising, stably introducing into a yeast host at least one DNA construct comprising, in proper reading frame an Fe-responsive transcriptional regulatory region from PpSEC10 comprising the sequence set forth in SEQ ID NO:1 or a fragment or variant thereof, a transcriptional initiation region, and a nucleotide sequence of interest, culturing said yeast host cell to generate cell mass, wherein the Fe concentration is sufficient to at least partially repress the expression of the nucleotide sequence of interest, reducing the concentration of Fe in the media to induce increased expression of the nucleotide sequence of interest, and further culturing the yeast host until a desired amount of the nucleotide sequence of interest or the polypeptide encoded by the DNA sequence is produced.

DETAILED DESCRIPTION OF THE INVENTION

The present invention is directed to methods and compositions for the expression of a nucleotide sequence of interest. The methods of the invention can also be used for the expression and isolation of polypeptides, for example, heterologous polypeptides, using a yeast host cell as the expression system. Compositions comprise isolated or purified nucleic acid sequences that comprise the nucleic acid sequences of the transcriptional regulatory element of the PpSEC10 gene (SEQ ID NO:1) and fragments and variants thereof.

The invention encompasses isolated or substantially purified nucleic acid or protein compositions. A "purified" nucleic acid molecule or protein, or biologically active portion thereof, is substantially free of other cellular material, or culture medium when produced by recombinant techniques, or substantially free of chemical precursors or other chemicals when chemically synthesized. A polypeptide that is substantially free of cellular material includes preparations of protein having less than about 30%, 20%, 10%, 5%, (by dry weight) of contaminating protein. When the polypeptide of the invention or biologically active portion thereof is recombinantly produced, preferably culture medium represents less than about 30%, 20%, 10%, or 5% (by dry weight) of chemical precursors or non-protein-of-interest chemicals. An "isolated" nucleic acid is free of sequences (preferably protein encoding sequences) that naturally flank the nucleic acid (i.e., sequences located at the 5' and 3' ends of the nucleic acid) in the genomic DNA of the organism from which the nucleic acid is derived. For example, in various embodiments, the isolated nucleic acid molecule can contain less than about 5 kb, 4 kb, 3 kb, 2 kb, 1 kb, 0.5 kb, or 0.1 kb of nucleotide sequences that naturally flank the nucleic acid molecule in genomic DNA of the cell from which the nucleic acid is derived.

The present invention provides methods to chemically regulate the PpSEC10 transcriptional control region by modulating the Fe concentration of the culturing medium. Hence the methods of the invention find use in regulating expression of a nucleotide sequence of interest. By "transcriptional control region" is intended the nucleotide sequences that control transcription. The transcriptional control region contains at least two domains. The first domain is a transcriptional initiation region, which includes the transcription initiation site, the TATA box, RNA capping sequences as appropriate, and an RNA polymerase binding site. The second domain of the transcriptional control region is the transcriptional regulatory region or upstream activating sequence (UAS). The transcriptional regulatory region may regulate transcription in a positive or negative manner resulting in either the enhancement or repression of transcription, respectively.

A transcriptional regulatory region (SEQ ID NO:1) within the transcriptional control region (SEQ ID NO:2) of the PpSEC10 nucleotide sequence has been identified by the inventors. The PpSEC10 regulatory region is located upstream of the transcription initiation site and is responsible for the Fe regulation of the PpSEC10 transcriptional initiation region. Methods to regulate the PpSEC10 transcriptional initiation region using the Fe-responsive transcriptional regulatory region are discussed in more detail below.

By "regulate" is intended either the repression or the activation of transcription from a transcriptional initiation region. By "Fe-responsive" is intended the ability of the transcriptional regulatory region of PpSEC10 to activate or repress transcription under either low or high Fe conditions, respectively. By "modulate Fe concentration" is intended an increase or a decrease in Fe concentration in the culture medium that results in regulation of expression of the nucleotide sequence of interest. The Fe concentration in the culture media used to repress the transcriptional initiation. region may range from about 5 $\mu$M to about 20 $\mu$M Fe, including for example 8, 12, 16, 18, or 20 $\mu$M Fe. The concentration of Fe in the media can be greater than 20 $\mu$M Fe, for example, up to any Fe concentration used in the art. The Fe concentration in the culture medium that activates the transcription initiation region needs only to be sufficient to meet the growth requirements of the cell. Such a concentration may range from about 4 $\mu$M to about 2 $\mu$M Fe, from about 2 $\mu$M to about 1 $\mu$M, or less than 1 $\mu$M Fe, including for example 4 $\mu$M, 3 $\mu$M, 2 $\mu$M, 1 $\mu$M, or 0.5 $\mu$M. In specific embodiments, Fe is present at the minimum concentration required for cell growth. In one embodiment, transcription is activated by the continuous addition of Fe to the culturing medium at the rate the cells consume it. It is recognized that by modulating Fe concentration, various levels of transcriptional activation or repression can be achieved.

Methods are provided for the chemical regulation of the PpSEC10 transcriptional initiation region using the Fe-responsive transcriptional regulatory region of PpSEC10. Therefore, the transcriptional control region of the PpSEC10 gene, and variants and fragments of these nucleotide and amino acid sequences are of particular interest for the purposes of this invention. Furthermore, the present invention provides methods to regulate expression of a nucleotide sequence of interest. In one embodiment the nucleotide sequence of interest encodes the SEC10 polypeptide. Therefore, the nucleotide sequences encoding the components of the precursor SEC10 polypeptide, their respective amino acid sequences, and variants and fragments of these nucleotide sequences and amino acid sequences are also of particular interest.

By "fragment" is intended a portion of the regulatory or coding nucleotide sequence or a portion of the amino acid sequence. Fragments of the transcriptional regulatory region and the transcriptional control region may retain their regulatory activity and their transcription initiation activity, respectively. Thus, for example, less than the entire PpSEC10 transcriptional regulatory region can be utilized to drive expression of an operably linked nucleotide sequence of interest, so long as the transcriptional regulatory region retains the ability to activate transcription under low Fe conditions and repress transcription under high Fe conditions. Any number of the 85 nucleotide may be used, for example, 15, 25, 50, 60, 65, 70, 75, 80, 85, or up to the entire 86 nucleotides of the PpSEC10 transcriptional regulatory region may be used to regulate expression of a coding sequence. It is within skill in the art to determine whether such fragments retain their regulating activity. For example, a DNA construct comprising, in proper reading frame, a PpSEC10 transcriptional regulatory region, a transcription initiation sequence, and a nucleotide sequence encoding a reporter sequence such as $\beta$-galctosidase, chloroamphenical acetyl transferase, luciferase, or Pho1, may be transformed into a host cell. Transcriptional regulation of the reporter gene by Fe can be determined by Northern analysis. See, for example, Boyer et al. (1998) *J. Bacteriology* 180(7):1662–72, Pastoricic et al. (1999) *J. Biol Chem* 274:24297–307; Rufo et al. (1999) *Biochem Biophys Res Commun* 261:400–5, and Experimental section, example 2, of this application.

Similarly, less than the entire PpSEC10 transcription initiation region may be used to drive expression of an operably linked nucleotide sequence of interest, so long as the initiation region retains the ability to initiate transcription. Any number of nucleotides can be used, for example, less than 15, 25, 50, 100, or up to the entire length of the PpSEC10 transcriptional initiation region may be used to regulate expression.

By "variant" is intended substantially similar sequences. Thus, for nucleotide sequences, variants include the sequences of the PpSEC10 transcriptional regulatory. region, and transcriptional initiation region and modifications thereof that continue to regulate expression. Variant nucleotide sequences also include synthetically derived nucleotide sequences that have been generated, for example, by site directed mutagenesis but which still retain the ability to regulate or initiate transcription. Generally, nucleotide sequence variants of the invention will have at least 70%, generally 80%, 85%, 90%, 91%, 92%, 93%, 94%, 95%, 96%, 97%, 98%, or 99% sequence identity to its respective native nucleotide sequence.

With respect to coding sequences, fragments of a nucleotide sequence may encode polypeptide fragments that retain the biological activity of the native mature SEC10p polypeptide. For example, a functional fragment of the SEC10p polypeptide retains the ability to bind the SEC10p antibody. A fragment of the SEC10p polypeptide may be 10, 20, 36, 40, 50, 70, 90, amino acids or up to the full length of the mature SEC10 polypeptide. Fragments of a coding nucleotide sequence may range from at least about 20, 24, 50, 100, 200, 300 nucleotides, and up to the entire 303 nucleotide sequence encoding the mature SEC10p polypeptide of the invention. Fragments of a nucleotide sequence that are useful as hybridization probes generally do not encode polypeptides that retain biological activity of the native polypeptide.

Variants of the nucleotide sequences that encode either the full length or mature SEC10p polypeptide include sequences that differ conservatively because of the degeneracy of the genetic code. These naturally occurring allelic variants can be identified with the use of well-known molecular biology techniques, such as polymerase chain reaction (PCR) and hybridization techniques as outlined below. Variant nucleotide sequences also include synthetically derived nucleotide sequences that have been generated, for example, by using site-directed mutagenesis but which still encode the mature SEC10p polypeptide sequences, as discussed below. Generally, nucleotide sequence variants of the invention will have at least 70%, at least 80%, at least 90 to 95% or more, or at least about 90%, 91%, 92%, 93%, 94%, 95%, 96%, 97%, 98%, or 99% identity to the native nucleotide sequence.

With respect to the amino acid sequences for the full length or mature SEC10p polypeptide, variants include those polypeptides that are derived from the native polypeptides by deletion (so-called truncation) or addition of one or more amino acids to the N-terminal and/or C-terminal end of the native polypeptide; deletion or addition of one or more amino acids at one or more sites in the native polypeptide; or substitution of one or more amino acids at one or more sites in the native polypeptide. Such variants may result from, for example, gene tic polymorphism or from human manipulation. Methods for such manipulations are generally known in the art.

For example, amino acid sequence variants of the polypeptide can be prepared by mutations in the cloned DNA sequence encoding the mature SEC10p polypeptide. Methods for mutagenesis and nucleotide sequence alterations are well known in the art. See, for example, Walker and Gaastra, eds. (1983) *Techniques in Molecular Biology* (MacMillan Publishing Company, New York); Kunkel (1985) *Proc. Natl. Acad. Sci. USA* 82:488–492; Kunkel et al. (1987) *Methods Enzymol.* 154:367–382; Sambrook et al. (1989) *Molecular Cloning: A Laboratory Manual* (2d ed., Cold Spring Harbor Laboratory Press, Plainview, N.Y.); U.S. Pat. No. 4,873,192; and the references cited therein; herein incorporated by reference. Guidance as to appropriate amino acid substitutions that may not affect biological activity of the mature SEC10p polypeptide may be found in the model of Dayhoff et al. (1978) *Atlas of Polypeptide Sequence and Structure* (Natl. Biomed. Res. Found., Washington, D.C.), herein incorporated by reference. Conservative substitutions, such as exchanging one amino acid with another having similar properties, may be preferred. Examples of conservative substitutions include, but are not limited to, Gly⇔Ala, Val⇔Ile⇔Leu, Asp⇔Glu, Lys⇔Arg, Asn⇔Gln, and Phe⇔Trp⇔Tyr.

In constructing variants of the mature SEC10p polypeptide, modifications to the nucleotide sequences encoding the variants will be made such that variant polypeptides may continue to possess the desired activity. Obviously, any mutations made in the DNA encoding a variant polypeptide must not place the sequence out of reading frame and preferably will not create complementary regions that could produce secondary mRNA structure.

Any of the nucleotide sequences used in the methods of the invention can be optimized for enhanced expression in the yeast host of interest. That is, these nucleotide sequences can be synthesized using yeast-preferred codons for improved expression. See for example, U.S. Pat. Nos. 5,219, 759 and 5,602,034.

Thus the nucleotide sequences for the transcriptional regulatory region, the transcriptional control region, and the coding region of PpSEC10 include the native forms as well as fragments and variants thereof. Likewise, the mature SEC10p polypeptide includes the native forms as well as fragments and variants thereof. The variant nucleotide sequences and variant polypeptides will be substantially identical and functionally equivalent to the native nucleotide sequences and native polypeptides, respectively. A variant of a native nucleotide sequence or native polypeptide has substantial identity to the native sequence or native polypeptide. A variant of a polypeptide may differ by as few as 1 to 10 amino acid residues, such as 6–10, as few as 5, as few as 4, 3, 2, or even 1 amino acid residue. A variant of a nucleotide sequence may differ by as low as 1 to 30 nucleotides, such as 6 to 20, as low as 5, as few as 4, 3, 2, or even 1 nucleotide residue.

By "sequence identity" is intended the same nucleotides or amino acid residues are found within the variant sequence and a reference sequence when a specified, contiguous segment of the nucleotide sequence or amino acid sequence of the variant is aligned and compared to the nucleotide sequence or amino acid sequence of the reference sequence. Methods for sequence alignment and for determining identity between sequences are well known in the art. See, for example, Ausubel et al., eds. (1995) *Current Protocols in Molecular Biology*, Chapter 19 (Greene Publishing and Wiley-Interscience, New York); and the ALIGN program (Dayhoff (1978) in *Atlas of Polypeptide Sequence and Structure* 5:Suppl. 3 (National Biomedical Research Foundation, Washington, D.C.). With respect to optimal alignment of two nucleotide sequences, the contiguous segment of the variant nucleotide sequence may have additional nucleotides or deleted nucleotides with respect to the reference nucleotide sequence. Likewise, for purposes of optimal alignment of two amino acid sequences, the contiguous segment of the variant amino acid sequence may have additional amino acid residues or deleted amino acid residues with respect to the reference amino acid sequence. The contiguous segment used for comparison to the reference nucleotide sequence or reference amino acid sequence will comprise at least 20 contiguous nucleotides, or amino acid residues, and may be 30, 40, 50, 100, or more nucleotides or amino acid residues. Corrections for increased sequence identity associated with inclusion of gaps in the variant's nucleotide sequence or amino acid sequence can be made by assigning gap penalties. Methods of sequence alignment are well known in the art.

The determination of percent identity between two sequences can be accomplished using a mathematical algorithm. Percent identity of an amino acid sequence is determined using the Smith-Waterman homology search algorithm using an affine 6 gap search with a gap open penalty of 12 and a gap extension penalty of 2, BLOSUM matrix 62. The Smith-Waterman homology search algorithm is taught in Smith and Waterman (1981) *Adv. Appl. Math* 2:482–489, herein incorporated by reference. Alternatively, percent identity of a nucleotide sequence is determined using the Smith-Waterman homology search algorithm using a gap open penalty of 25 and a gap extension penalty of 5. Such a determination of sequence identity can be performed using, for example, the DeCypher Hardware Accelerator from TimeLogic Version G.

It is further recognized that when considering percentage of amino acid identity, some amino acid positions may differ assa result of conservative amino acid substitutions, which do not effect properties of polynucleotide function. In these instances, percent sequence identity may be adjusted upwards to account for the similarity in conservatively substituted amino acids. Such adjustments are well known in the art. See, for example, Meyers et al. (1988) *Computer Applic. Biol. Sci.* 4:11–17.

By "functionally equivalent" is intended that the variant nucleotide sequence defines a transcriptional control region or encodes an amino acid sequence for a polypeptide that has substantially the same function as the native transcriptional control region or native polypeptide, respectfully. A variant of a nucleotide sequence for a PpSEC10 transcriptional regulatory regionwill retain the ability to regulate transcription. In one embodiment, the regulatory sequences will repress transcription in the presence of high Fe concentrations and activate transcription in the presence of low Fe concentration. A variant of a nucleotide sequence for a PpSEC10 transcription initiation region will retain the ability to initiate transcription. Similarly, a variant of the SEC10p polypeptide will possess the ability of the mature SEC10p to interact with a SEC10 antibody.

Functionally equivalent sequences of the present invention also encompass those fragments of the PpSEC10-derived transcriptional control nucleotide sequences and those fragments of the SEC10p mature polypeptide sequences that retain substantially the same function as the respective native sequence. For example, a functionally equivalent fragment of a nucleotide sequence containing the transcriptional regulatory region, when operably linked to a transcriptional initiation region, will drive expression of an operably linked nucleotide sequence. Such fragments will comprise at least about 15 contiguous nucleotides, at least about 20 contiguous nucleotides, at least about 24, 50, 60, 65, 70, 75, 80, 85 or up to the entire 86 contiguous nucleotides of the transcriptional regulatory region of the PpSEC10 gene. The nucleotides of such fragments will retain the ability to regulate transcription, more specifically, repress transcription in the presence of high Fe concentrations and activate transcription in the presence of low Fe concentrations. Such fragments may be obtained by use of restriction enzymes to cleave the native PpSEC10 transcriptional control element; by synthesizing a nucleotide sequence from the native nucleotide sequence of the regulatory region; or may be obtained through the use of PCR technology. See particularly Mullis et al. (1987) *Methods Enzymol.* 155:335–350, and Erlich, ed. (1989) *PCR Technology* (Stockton Press, New York). Again, variants of these transcriptional regulatory fragments, such as those resulting from site-directed mutagenesis, are encompassed by the methods of the present invention.

Methods are available in the art for determining functional equivalence. The activity of the transcriptional regulatory region and transcriptional initiation regions may be measured by Northern blot analysis. See, for example, Sambrook et al. (1989) *Molecular Cloning: A Laboratory Manual* (2d ed., Cold Spring Harbor Laboratory Press, Plainview, N.Y.), herein incorporated by reference. Biological activity can be measured using assays specifically designed for measuring activity of a native polypeptide. Furthermore, antibodies raised against the biologically active native SEC10p polypeptide can be tested for their ability to bind to the functionally equivalent variant, where effective binding is indicative of a polypeptide having a conformation similar to that of the native polypeptide.

The PpSEC10-derived regulatory sequences of the invention, and fragments and variants thereof, can be used as probes for the isolation of corresponding homologous sequences in other organisms, more particularly other yeasts. In this manner, methods such as PCR, hybridization, and the like can be used to identify such sequences having substantial sequence identity to the sequences of the invention. See, for example, Sambrook et al. (1989) *Molecular Cloning: A Laboratory Manual* (2d ed., Cold Spring Harbor Laboratory Press, Plainview, N.Y.) and Innis et al. (1990), *PCR Protocols: A Guide to Methods and Applications* (Academic Press, New York). Nucleic acid sequences isolated based on their sequence identity to the *Pichia pastoris* PpSEC10 regulatory region set forth herein or to fragments and variants thereof are encompassed by the present invention.

In a PCR method, pairs of primers can be used in PCR reactions for amplification of DNA sequences from cDNA or genomic DNA extracted from any organism of interest. In addition, a single specific primer with a sequence corresponding to one of the nucleotide sequences disclosed herein can be paired with a primer having a sequence of the DNA vector in the cDNA or genomic libraries for PCR amplification of the sequences 5' or 3' to the nucleotide sequences disclosed herein. Similarly, nested primers may be used instead of a single specific primer for the purposes of the invention. Methods for designing PCR primers and PCR cloning are generally known in the art and are disclosed in Sambrook et al. (1989) *Molecular Cloning: A Laboratory Manual* (2d ed., Cold Spring Harbor Laboratory Press, Plainview, N.Y.). See also Ignis et al., eds. (1990) *PCR Protocols: A Guide to Methods and Applications* (Academic Press, New York).

In a hybridization method, all or part of a known nucleotide sequence can be used to screen cDNA or genomic libraries made from other organisms of interest. Methods for construction of such cDNA and genomic libraries are generally known in the art and are disclosed in Sambrook et al. (1989) *Molecular Cloning: A Laboratory Manual* (2d ed., Cold Spring Harbor Laboratory Press, Plainview, N.Y.). The so-called hybridization probes maybe genomic DNA fragments, cDNA fragments, RNA fragments, or other oligonucleotides, and may be labeled with a detectable group such as $^{32}P$, or any other detectable marker. Probes for hybridization can be made by labeling synthetic oligonucleotides based on the known nucleotide sequence of interest. Degenerate primers designed on the basis of conserved nucleotides or amino acid residues in the known nucleotide or encoded amino acid sequence can additionally be used. Preparation of probes for hybridization is generally known in the art and is disclosed in Sambrook et al. (1989) *Molecular Cloning: A Laboratory Manual* (2d ed., Cold Spring Harbor Laboratory Press, Plainview, N.Y.), hereby incorporated by reference.

Using hybridization techniques, all or part of the PpSEC10 regulatory nucleotide sequence is used as a probe that selectively hybridizes to other possible regulatory nucleotide sequences present in a population of cloned genomic DNA fragments or cDNA fragments (i.e., genomic or cDNA libraries) from a chosen organism. To achieve specific hybridization under a variety of conditions, such probes include sequences that are unique and are preferably at least about 20 nucleotides in length, and most preferably at least about 40, 50, 60, 70, or 75 nucleotides in length. This technique may be used to isolate other possible PpSEC10 regulatory nucleotide sequences from a desired organism or as a diagnostic assay to determine the presence of a PpSEC10 regulatory nucleotide sequence in an organism. Hybridization techniques include hybridization screening of plated DNA libraries (either plaques or colonies; see, for example, Innis et al., eds. (1990) *PCR Protocols: A Guide to Methods and Applications* (Academic Press, New York)).

Thus, in addition to the native nucleotide sequences and fragments and variants thereof, the isolated nucleotide sequences of the invention also encompass homologous DNA sequences identified and isolated from other organisms or from *Pichia pastoris* by hybridization with entire or partial sequences obtained from the *Pichia pastoris* PpSEC10-derived regulatory sequences of the invention or variants thereof. Conditions that will permit other DNA sequences to hybridize to the DNA sequences disclosed herein can be determined in accordance with techniques generally known in the art. For example, hybridization of such sequences may be carried out under conditions of reduced stringency, medium stringency, or high stringency conditions.

Stringent wash conditions are well known and understood in the art and are disclosed, for example, in Sambrook et al. (1989) *Molecular Cloning: A Laboratory Manual*, 2d ed.: 9.50–9.51. Typically, for stringent hybridization conditions, a combination of temperature and salt concentration should be chosen that is approximately 12–20° C. below the calculated $T_m$ of the hybrid under study. The $T_m$ of a hybrid between a nucleotide sequence of the invention and a polynucleotide sequence which is 65%, 75%, 85%, 90%, 95%, 96%, 97%, 98%, or 99% identical can be calculated, for example, using the equation of:

$$T_m = 81.5°\ C. - 16.6(\log_{10}[Na^+]) + 0.41(\%\ G+C) - 0.63(\%\text{formamide}) - 600/l),$$

where l is the length of the hybrid in basepairs (Bolton et al. (1962) *Proc. Natl. Acad. Sci. U.S.A.* 48:1390). Stringent wash conditions include, for example, 4×SSC at 65° C., or 50% formamide, 4×SSC at 42° C., or 0.5×SSC, 0.1% SDS at 65° C. Highly stringent wash conditions include, for example, 0.2×SSC at 65° C. Stringent hybridization conditions further include hybridizing at 68° C. in 5×SSC, 5×Denhart's solution, 0.1% SDS and washing in 0.2×SSC and 0.1% SDS at room temperature. The duration of hybridization is generally less than about 24 hours and usually about 4 to 12 hours. See Sambrook et al. (1989) *Molecular Cloning: A Laboratory Manual* (2d ed., Cold Spring Harbor Laboratory Press, Plainview, N.Y.).

The PpSEC10 transcriptional regulatory nucleotide sequences and variants and fragments thereof, find use in methods directed to the expression of a nucleotide sequence of interest in a yeast host cell. In one embodiment of the present invention, the transcriptional regulatory region of the PpSEC10 gene or fragment or variant thereof, is used to regulate expression of an operably linked nucleotide sequence encoding a polypeptide of interest. Specifically, the present invention provides methods to chemically regulate the PpSEC10 transcriptional initiation element or a heterologous transcriptional initiation element by modulating the Fe concentration of the culturing medium.

The nucleotide sequence of interest operably linked to the PpSEC10 transcription control region may be provided in a DNA construct, particularly, a recombinant DNA construct, for introduction into a yeast host cell. By "recombinant" is intended genetic engineering of DNA fragments, which are assembled into the DNA construct of interest. These DNA constructs comprise all of the elements necessary for expression of a nucleotide sequence of interest in a yeast host cell. The DNA constructs can further comprise any elements necessary for the secretion of a polypeptide encoded by the nucleotide sequence of interest. Thus, the DNA constructs of the invention, when introduced into a yeast host cell, can be expressed within that yeast host cell. Each DNA construct is provided with a plurality of restriction sites for insertion of the nucleotide sequence of interest such that the sequences will be under the transcriptional regulation of the regulatory regions of the DNA construct. The DNA construct may additionally contain selectable marker genes, such as the *Pichia pastoris* histidinol dehydrogenase (HIS4) gene, to facilitate selection of stably transformed cells.

Such a recombinant DNA construct comprises in proper reading frame the following operably linked components: a nucleotide sequence comprising the PpSEC10 transcriptional regulatory region, or variant or fragment thereof; a yeast-recognized transcriptional initiation region; a nucleotide sequence of interest; and, a nucleotide sequence for a yeast-recognized transcription termninator. By "operably linked" is intended the individual nucleotide sequences are joined such that expression of the nucleotide sequence of interest is under the regulatory control of the transcriptional control and terminator sequences. When the nucleotide sequence of interest encodes a polypeptide, "operably linked" further encompasses the joining of the nucleotide sequences such that expression of the coding sequences occurs in the proper reading frame.

The transcriptional initiation region may be the PpSEC10 transcriptional initiation or a heterologous yeast-recognized transcriptional initiation region. By "heterologous yeast-recognized transcriptional initiation" region is intended any initiation region that is functional in yeast and foreign to the regulatory region set forth in SEQ ID NO:1. The heterologous regions may be either native (i.e., endogenous) to the yeast host cell or the region may be foreign to the host cell. A "hybrid" transcriptional control region is formed when the transcriptional regulatory region of SEQ ID NO:1 is operably linked to a heterologous transcriptional initiation region. By "yeast-recognized" is intended the initiation region is functional in the yeast host cell.

Synthetic hybrid transcriptional control regions are known it the art. Such regions comprise the transcription regulatory region of one yeast transcriptional control element operably linked to the transcription initiation region of a heterologous yeast transcriptional control element. In an embodiment of the invention, gene expression is controlled by a synthetic hybrid transcriptional control element comprising the Fe-responsive transcriptional regulatory region of SEQ ID NO:1 operably linked to the transcription initiation region of a heterologous yeast-recognized transcription control element. The transcriptional initiation region used in the hybrid transcriptional control element may include any yeast-recognized transcriptional initiation region. Examples of such regions include but are not limited to, the transcriptional initiation elements of a glycolytic enzyme such as glyceraldehyde-3-phosphate dehydrogenase, pyruvate kinase, alcohol dehydrogenase, phosphoglucoisomerase, triose phosphate, and phosphofructo kinase. These nucleotide sequences are available in the art. See, for example, EPO Publication No. 164,556 and U.S. Pat. No. 4,876,197 herein incorporated by reference. Additional regions include the transcriptional initiation region from the dihydroxyacetone synthase (DHAS) (Acc. No. X02424), alcohol oxidase 2 (AOX2) (Acc. No. X79871), and alcohol oxidase (AOX1) (Acc. No. E06612).

In another embodiment, the recombinant DNA construct comprises in proper reading frame the following operably linked components: a nucleotide sequence comprising a PpSEC10 transcriptional control region which lacks the Fe responsive regulatory region (SEQ ID NO:5); a nucleotide sequence of interest; and, a nucleotide sequence for a yeast-recognized transcription terminator.

By "yeast-recognized" terminator sequences are intended regulatory regions that are functional in the yeast host cell. Such sequences may be native (i.e., analogous) or foreign (i.e., heterologous) to the yeast cell or to the transcriptional regulatory region of SEQ ID NO:1. Thus in one embodiment, the terminator is the PpSEC10 terminator or a variant or fragment thereof. Alternatively, the terminator may be another yeast-recognized terminator, such as those for the α-factor polypeptide (U.S. Pat. No. 4,870,008) and the glycolytic enzymes mentioned above.

When the nucleotide sequence of interest encodes a polypeptide, the DNA construct may further comprise a nucleotide sequence encoding a yeast-derived secretion leader that serves to direct the polypeptide sequence of interest through the secretory pathway of the yeast host cell and is essential to bring about extracellular secretion of a polypeptide. Thus, in one embodiment of the invention, this secretion leader is the PpSEC10 secretion leader.

Alternatively, a yeast secretion leader derived from another yeast-secreted polypeptide may be used to direct the polypeptide encoded by the nucleotide sequence of interest through the secretory pathway of the yeast host cell. Such a yeast-derived secretion leader may be a naturally occurring secretion leader comprising its native secretion signal, or the secretion leader may be a synthetic hybrid comprising a secretion signal derived from a different yeast-secreted polypeptide. The yeast-secreted polypeptide that serves as a source for the secretion leader may be foreign or native to the yeast host cell. A number of secretion signals are well known in the art. Examples of secretion signals appropriate for the present invention include, but are not limited to, the secretion signal for α-factor (see, for example, U.S. Pat. No. 5,602,034; Brake et al. (1984) *Proc. Natl. Acad. Sci. USA* 81:4642:4646); invertase (WO 84/01153); PHO5 (DK 3614/83); YAP3 (yeast aspartic protease 3; PCT Publication No. 95/02059); and BAR1 (PCT Publication No. 87/02670). Alternatively, the secretion signal may be determined from, genomic or cDNA libraries using hybridization probe techniques available in the art (see Sambrook et al. (1989) *Molecular Cloning: A Laboratory Manual* (2d ed., Cold Spring Harbor Laboratory Press, Plainview, N.Y.), or even synthetically derived (see, for example, WO 92/11378).

During entry into the ER, the secretion signal is cleaved off the precursor polypeptide at a processing site. The processing site can comprise any peptide sequence that is recognized in vivo by a yeast proteolytic enzyme. This processing site may be the naturally occurring processing site for the secretion signal. More preferably, the naturally occurring processing site will be modified, or the processing site will be synthetically derived, so as to be a preferred processing site. By "preferred processing site" is intended a processing site that is cleaved in vivo by a yeast proteolytic enzyme more efficiently than is the naturally occurring site. Examples of preferred processing sites include, but are not limited to, dibasic peptides, particularly any combination of the two basic residues Lys and Arg, that is Lys-Lys, Lys-Arg, Arg-Lys, or Arg-Arg, most preferably Lys-Arg. These sites are cleaved by the protease encoded by the KEX2 gene of *Saccharomyces cerevisiae* (see Fuller et al. *Microbiology* 1986:273–278) or the equivalent protease of other yeast species (see Julius et al. (1983) *Cell* 32:839–852). In the event that the Kex2 protease would cleave a site within the polypeptide sequence encoded by the nucleotide sequence of interest, other preferred processing sites could be utilized such that the peptide sequence of interest remains intact (see, for example, Samnbrook et al. (1989) *Molecular Cloning: A Laboratory Manual* (2d ed., Cold Spring Harbor Laboratory Press, Plainview, N.Y.).

For purposes of the present invention, the secretion leader preferably comprises its native secretion signal, as in the case of the PpSEC10 leader. The α-factor polypeptide is another yeast-secreted polypeptide that may serve as an alternative source of secretion leader comprising its native secretion signal. A number of genes encoding precursor α-factor polypeptides have been cloned and their secretion leader peptide sequences identified. See, for example, Singh et al. (1983) *Nucleic Acids Res.* 11:4049–4063; Kudjan et al., U.S. Pat. Nos. 4,546,082; 5,010,182; herein incorporated by reference. α-factor secretion leaders comprising their native secretion signals have been used to express heterologous polypeptides in yeast. See, for example, Elliott et al. (1983) *Proc. Natl. Acad. Sci. USA* 80:7080–7084; Bitter et al. (1984) *Proc. Natl. Acad. Sci.* 81:5330–5334; Smith et al. (1985) *Science* 229:1219–1229; and U.S. Pat. Nos. 4,849,407 and 5,219,759; herein incorporated by reference.

When secretion of the polypeptide is desired, the nucleotide sequence of interest encoding the polypeptide is located in the DNA construct adjacent, preferably 3', to the nucleotide sequence encoding a secretion leader. Expression of the coding sequences for the yeast secretion leader and the heterologous polypeptide produces a hybrid precursor polypeptide, or so-called fusion polypeptide. By "hybrid" precursor polypeptide is intended the coding sequence for the secretion leader is foreign to the coding sequence for the desired polypeptide, and hence the two coding sequences are not natively expressed as a precursor polypeptidein the yeast host cell.

The hybrid precursor polypeptide comprises the necessary yeast-derived peptide sequences for movement of the desired polypeptide sequence through the secretory pathway of the yeast host cell. Preferably the nucleotide sequence encoding the yeast secretion leader will terminate in a yeast-recognized processing site, such as a dibasic processing site such as Lys-Arg or Arg-Arg recognized in vivo by a Kex2 protease, such that the secretion leader is cleaved off of the secreted desired polypeptide. For example, the SEC10 secretion leader terminates in this type of dibasic processing site. One of skill in the art will recognize that the hybrid precursor polypeptide may contain an additional coding sequence for another polypeptide of interest, such that the secreted polypeptide itself is a fusion polypeptide comprising two polypeptides joined by a peptide bond.

The recombinant DNA constructs comprising the nucleotide sequence of interest operably linked to the various regulatory regions discussed above, may also contain at least one additional nucleotide sequence of interest to be cotransformed into the yeast host. Alternatively, the additional nucleotide sequences of interest can be provided on a recombinant DNA construct other than the one comprising the transcriptional regulatory element sequence of SEQ ID NO:1. Where appropriate, the nucleotide sequence encoding the hybrid precursor polypeptide and any additional nucleotide sequences of interest may be optimized for increased expression in the transformed yeast, as previously noted.

Additional sequence modifications are known to enhance expression of nucleotide sequences in a cellular host. These include elimination of sequences encoding spurious polyadenylation signals, exon-intron splice site signals, transposon-like repeats, and other such well-characterized sequences that may be deleterious to gene expression. The G-C content of the sequence may be adjusted to levels average for a given cellular host, as calculated by reference to known genes expressed in the host cell. When possible, the nucleotide sequence is modified to avoid predicted hairpin secondary mRNA structures.

In preparing the recombinant DNA construct, the various nucleotide sequence fragments may be manipulated so as to provide for the sequences in the proper orientation and, as appropriate, in the proper reading frame. Toward this end, adapters or linkers may be employed to join the nucleotide fragments or other manipulations may be involved to provide for convenient restriction sites, removal of superfluous nucleotides, removal of restriction sites, or the like. For this purpose, in vitro mutagenesis, primer repair, restriction, annealing, resubstitutions, e.g., transitions and transversions, may be involved. See particularly Sambrook et al. (1989) *Molecular Cloning: A Laboratory Manual* (2d ed., Cold Spring Harbor Laboratory Press, Plainview, N.Y.).

The nucleotide sequences may be inserted into the DNA construct using standard recombinant DNA methods. The nucleotide sequence of interest may be identical to a naturally occurring sequence or may contain modifications. Such modifications can, for example, alter the physicochemical properties of the polypeptide encoded by the sequence, such as stability, activity, affinity for a particular ligand or receptor, antigenicity, therapeutic utility, or ability to be secreted from the host cell. Thus, the nucleotide sequence of interest encoding a mature polypeptide may be a variant or fragment as previously defined above.

The nucleotide sequence of interest may be an endogenous gene in the yeast host cell or may be a heterologous sequence. In specific embodiments, the nucleotide sequence of interest encodes the endogenous SEC10 polypeptide, or a variant or fragment thereof. By "heterologous" is intended a nucleotide sequence not normally found in the host cell. It may encode a precursor polypeptide form of the polypeptide, and hence contain the native secretion signal and/or secretion leader. Alternatively, it may encode the mature form of the polypeptide. In those instances where the nucleotide sequence encodes the precursor polypeptide form, modification of the native secretion leader to terminate in a yeast recognized processing site may facilitate secretion of the mature form of the polypeptide of interest in a biologically active, properly folded conformation. See the application entitled "Method for Expression of Heterologous Polypeptides in Yeast," U.S. Pat. No. 6,017,231, herein incorporated by reference.

The heterologous nucleotide sequence of interest may, for example, encode any polypeptide, fragment or variant thereof having a therapeutic or industrial use. Such polypeptides, include, but are not limited to, a structural polypeptide, an enzyme, a growth factor, a receptor for a ligand, an antibody, a hormone, a transport polypeptide, a storage polypeptide, a contractile polypeptide, a cell differentiation factor, a repressor, a transcription factor, a cytokine, a haematopoietic factor, or a novel engineered polypeptide. Illustrative polypeptides of interest include, but are not limited to, hormones and factors, such as insulin-like growth factor (IGF-I, IGF-II), platelet-derived growth factor (PDGF), growth hormone, somatomedins, epidermal growth factor (EGF), keratinocyte growth factor (KGF), fibroblast growth factor (FGF), nerve growth factor (NGF), TGF-beta, vascular endothelial cell growth factor (VEGF), luteinizing hormone, thyroid-stimulating hormone, epithelin precursor, epithelin 1, epithelin 2, oxytocin, insulin, vasopressin, renin, calcitonin, follicle-stimulating hormone, prolactin, erythropoietin (EPO), colony-stimulating factor (CSF), lymphokines such as interleukin-2, globins, immunoglobulins, interferons, enzymes, β-endorphin, enkephalin, dynorphin, etc.

In preferred embodiments the heterologous polypeptide of interest is IGF-1. Methods for the production of recombinant IGF-1 in yeast cells are known in the art. See for example, U.S. Pat. Nos. 5,612,198 and 5,324,639 herein incorporated by reference.

The polypeptide of interest may also be a fusion polypeptide consisting of two or more polypeptide fragments fused together by means of peptide bond. In this manner, the first polypeptide segment may comprise at least 6, 8, 10, 12, or 15 contiguous amino acids from the amino acid sequence, or may comprise up to the full-length amino acid sequence for the mature polypeptide. Techniques for making fusion polypeptides, either recombinantly or by covalently linking two polypeptide segments, are well known in the art. Thus the nucleotide sequence encoding the polypeptide of interest may comprise the coding sequence for a polypeptide in proper reading frame with a nucleotide sequence encoding the second polypeptide segment. The second polypeptide segment may be a full-length polypeptide or a polypeptide fragment. The second polypeptide or polypeptide fragment may be labeled with a detectable marker, such as an antibody tag, or may be an enzyme that will generate a detectable product. Enzymes suitable for this purpose, such as β-galactosidase, are well known in the art.

The DNA construct may further comprise a proteolytic or chemical cleavage site between the two heterologous polypeptide segments. Proteolytic or chemical cleavage sites are described in U.S. Pat. Nos. 5,935,824, and 5,459,051 herein incorporated by reference. Such sites include the cleavage recognition sequences of various site specific endoproteases, including but not limited to, papain, protease VIII, clostropain, trypsin, kallikrein, thrombin, factor Xa, renin, collagenase, and ubiquitin hydrolases. Furthermore, a linker or spacer sequence may be added between the cleavage site and the polypeptide coding sequences to facilitate efficient cleavage. Examples of such spacer sequences may be found in U.S. Pat. No. 5,935,824, herein incorporated by reference.

The DNA construct of the present invention can be ligated into a replicon (e.g., plasmid, cosmid, virus, mini-chromosome), thus forming an expression vector that is capable of autonomous DNA replication in vivo. Such autonomously replicating vectors comprise yeast autonomous replication sequences and 2μ-based vectors. Preferably the replicon will be a plasmid. Such a plasmid expression vector will be maintained in one or more replication systems, preferably two replications systems, one that allows for stable maintenance within a yeast host cell for expression purposes, and one that provides for stable propagation within a prokaryotic host for cloning purposes. Examples of such yeast-bacteria shuttle vectors include Yep24 (Botstein et al. (1979) Gene 8:17–24; pCl/1 (Brake et al. (1984) *Proc. Natl. Acad. Sci. USA* 81:4642–4646), and Yrp17 (Stnichomb et al. (1982) *J. Mol. Biol.* 158:15:7). For cloning purposes, the plasmid vector comprising a recombinant DNA construct assembled with PpSEC10 nucleotide sequences of the present invention may be introduced into suitable host cells using a variety of techniques which are available in the art. These techniques include, but are not limited to, transferrin-polycation-mediated DNA transfer, transfection with naked or encapsulated nucleic acids, liposome-mediated cellular fusion, intracellular transportation of DNA-coated latex beads, protoplast fusion, viral infection, electroporation, calcium phosphate-mediated transfection, and lithium salt-mediated transformation.

Additionally, a plasmid expression vector may be a high or low copy number plasmid, the copy number generally ranging from about 1 to about 200. With high copy number yeast vectors, there will generally be at least 10, preferably at least 20, and usually not exceeding about 250 copies in a single host. Either a high or low copy number vector may be desirable, depending upon the effect of the vector and of expression of the polypeptide of interest on the host. See, for example, Brake et al. (1984) *Proc. Natl. Acad. Sci. USA* 81:4642–4646.

More preferably, the recombinant DNA construct is ligated into a plasmid vector that allows for integration of the construct into the yeast genome. Examples of such integrating vectors are known in the art. See, for example, Botstein et al. (1979) *Gene* 8:17–24. Use of integrating vectors maximizes the stability of foreign polypeptide production in a yeast host cell (Romanos et al. (1992) *Yeast* 8:423–488). Such a vector further comprises two segments of yeast host DNA sequences. For example, the DNA construct may be flanked with homologous regions of a yeast gene, such as the *Pichia pastoris* HIS4 gene, so that the construct can be integrated into the yeast genome by means of homologous recombination. The vector is linearized with a restriction enzyme, and the linearized DNA stimulates single crossover-type integration with the yeast host cell DNA.

Yeast host cells harboring multiple integrated copies of a recombinant DNA construct of the present invention may be generated by methods well known in the art. At least two such approaches have been developed. The first relies upon identifying multicopy strains that arise naturally as a low percentage of transformed cell populations. In this manner, large numbers of transformants are screened for production levels of the polypeptide of interest by SDS-polyacrylamide gel electrophoresis, immunoblotting, or screened for multiple copies of the foreign gene using colony dot-blot hybridization. Alternatively, multiple copies of the recombinant DNA construct are constructed within a single vector prior to transformation of the yeast host cells. See, for example, Cregg et al. (1993) *Bio/Technology* 11:905–910, for a review of these methods. When a single vector is constructed with multiple copies of a DNA construct of the present invention, it may contain about 3 copies, preferably about 6 copies, more preferably about 8 copies of a particular DNA construct. It is within skill in the art to determine the optimal number of DNA constructs for a given polypeptide of interest and for a given strain of yeast.

The yeast cell to be transformed with an expression vector comprising at least one copy of a recombinant DNA construct that comprises the PpSEC10 transcriptional regulatory nucleotide sequence, a transcriptional initiation region, and a nucleotide sequence of interest can be any yeast cell. Alternatively, a nucleotide sequence of interest can be introduced into the yeast cell such that the sequence is operably linked to the endogenous PpSEC10 promoter. Such methods comprise introducing into the yeast cell a DNA construct comprising the nucleotide sequence of interest flanked at both the 5' and 3' ends by nucleic acid sequences that direct homologous recombination downstream of the PpSEC10 transcriptional control region. Methods of generating DNA constructs for use in such homologous recombination events are well known in the art. See, for example, Chanda et al. (1994) *Current Protocols in Molecular Biology,* Vol 2 John Wiley and Sons Inc., herein incorporated by reference.

By "yeast" is intended ascosporogenous yeasts (Endomycetales), basidiosporogenous yeasts, and yeast belonging to the Fungi Imperfecti (Blastomycetes). The ascosporogenous yeasts are divided into two families, Spermophthoraceae and Saccharomycetaceae. The later is comprised of four subfamilies, Schizosaccharomycoideae (e.g., genus Schizosaccharomyces), Nadsonioideae, Lipomycoideae, and Saccharomycoideae (e.g., genera Pichia, Kluyveromyces, and Saccharomyces). The basidiosporogenous yeasts include the genera Leucosporidium, Rhodosporidium, Sporidiobolus, Filobasidium, and Filobasidiella. Yeast belonging to the Fungi Imperfecti are divided into two families, Sporobolomycetaceae (e.g., genera Sporobolomyces, Bullera) and Cryptococcaceae (e.g., genus Candida). Since the classification of yeast may change in the future, for the purposes of this invention, yeast shall be defined as described in Skinner et al., eds. (1980) *Biology and Activities of Yeast* (Soc. App. Bacteriol. Symp. Series No. 9). In addition to the foregoing, those of ordinary skill in the art are presumably familiar with the biology of yeast and the manipulation of yeast genetics. See, for example, Bacila et al., eds. (1978) *Biochemistry and Genetics of Yeast;* Rose and Harrison, eds. (1987) *The Yeasts* ($2^{nd}$ ed.); Strathern et al., eds. (1981) *The Molecular Biology of the Yeast Saccharomyces;* herein incorporated by reference.

The selection of suitable yeast for the practice of the present invention is within the skill of the art. When selecting yeast hosts for expression, suitable hosts may include those shown to have, for example, good secretion capacity and low proteolytic activity. Protease-deficient strains of *P. pastoris* are known in the art. See, for example, U.S. Pat. No. 5,612,198 and references cited therein. In general, protease deficient strains. may be generated by the disruption of *P. pastoris* genes, such as PEP4 or PRB-1, which encode polypeptides that directly or indirectly affect the protease activity of the cell. Some of the protease activities disrupted include, for example, polypeptidease A, polypeptidease B, and carboxypeptidase Y activities. Yeast are generally available from a variety of sources, including the Yeast Genetic Stock Center, Department of Biophysics and Medical Physics, University of California, Berkeley, Calif.; and the American Type Culture Collection, Rockville, Md.

Of particular interest to the present invention are species within the genera Pichia, Kluyveromyces, Saccharomyces, Schizosaccharomyces, and Candida. Species of particular interest include *Pichia pastoris, Kluyveromyces lactis,* and the Saccharomyces species *S. cerevisiae, S. carlsbergensis, S. diastaticus, S. douglasii, S. kluyveri, S. norbensis,* and *S. oviformis.*

The yeast host undergoing transformation to express the nucleotide sequence of interest may be a mutant *Pichia pastoris* strain that has a disabled PpSEC10 gene in its genome. See Publication No. WO 99/24062 entitled "Novel *Pichia Pastoris* Gene Sequence and Methods for Their Use," herein incorporated by reference.

Methods of introducing exogenous DNA into yeast hosts are well known in the art. There are a number of ways to transform yeast. For example, spheroplast transformation is taught by Hinnen et al. (1978) *Proc. Natl. Acad. Sci. USA* 75:1919–1933 and Stinchcomb et al., EPO Publication No. 45,573; herein incorporated by reference. Transformants are grown in an appropriate nutrient medium, and, where appropriate, maintained under selective pressure to insure retention of endogenous DNA.

Methods of culturing yeast cells in both small and large volume (i.e., fermentation) cultures are well known in the art. For example, the yeast *Pichia pastoris* may be cultured at cell densities greater than 100 g/liter dry weight. At least 0.3 g/l of a desired polypeptide may be produced. Preferably, 0.5, 1.0, 2.5, 8.0, or 12 g/l of the desired polypeptide is produced. Small-scale cultures of yeast cells comprising a recombinant DNA construct of the present invention may be screened for those cells that either express higher levels of the nucleotide sequence of interest or produce larger amounts of the polypeptide encoded by the sequence of interest. Such screening is routine in the art. Components of the culture medium, such as the carbon or nitrogen sources, may be varied to increase the level of nucleotide expression or the amount of desired polypeptide secreted. When the PpSEC10 transcriptional regulatory element is used to regulate expression of a nucleotide sequence of interest, the carbon source in the medium may be, for example, glucose, glycerol, or methanol. Secretion of the polypeptide can be enhanced by the addition of casein amino acids to the medium. Preferably, the medium contains a 2× yeast nitrogen base.

The present invention provides a method to regulate transcription by modulating the Fe concentration of the culture media. Specifically, methods are provided to activate and repress expression of a nucleotide sequence operably linked to a transcriptional control region comprising the PpSEC10 transcription regulatory element operably linked to a transcription initiation region. Optimal expression conditions will result in the maximum expression of the nucleic acid sequence of interest. When the nucleotide sequence of interest encodes a polypeptide, optimal expression conditions result in a maximum yield of the polypeptide of interest and a minimization of proteolytic degradation products.

Expression of a heterologous polypeptide in a host cell is often detrimental to the host cell. In some instances, the heterologous polypeptide may negatively affect the physiology of the host cell. In other instances, the overexpression of the heterologous polypeptide may be unduly taxing for the producing cells. In such instances, optimal conditions for heterologous polypeptide production in a host cell are achieved by controlling separately cell growth and polypeptide production from the nucleotide sequence of interest.

The Fe-responsive PpSEC10 transcription regulatory region allows the cell growth phase and the production phase to be separated. The growth phase is characterized by culturing the host cells under conditions that allow cell mass to be generated. During the growth phase, host cells are cultured in media having sufficiently high Fe concentrations such that the PpSEC10 transcriptional regulatory region represses transcription, and thus, the nucleotide sequence of interest is not expressed. Sufficiently high Fe concentrations that repress transcription range from about 5 $\mu$M Fe to about 20 $\mu$M Fe. For example, the Fe concentration can be 8, 10, 12, 14, 16, or 18 $\mu$M Fe. Furthermore, the Fe concentration in the media can be greater than 20 $\mu$M (i.e., up to the Fe levels used in the art).

The production phase is characterized by culture conditions that result in expression of the nucleotide sequence of interest and little additional cell growth. During the production phase, the host cells are cultured in medium having sufficiently low Fe concentration such that the PpSEC10 regulatory region activates transcription. Expression of the operably linked nucleotide sequence of interest results. Sufficiently low Fe concentration may range from about 4 $\mu$M to about 2 $\mu$M, from about 2 $\mu$M to about 1 $\mu$M, more preferably less than 1 $\mu$M, and most preferably Fe is present at the minimal concentration required for cell growth. In one preferred embodiment, Fe is continuously added to the culture media at the same rate the Fe is consumed by the cells.

Additional culture conditions that will impact polypeptide yield and degradation include, for example, medium buffering that is adequate for the culture density and adjusted to a pH that minimizes proteolytic degradation of the polypeptide product and maximum aeration. Furthermore, addition of a modest amount of peptone or casamino acids may protect the polypeptide of interest from proteolysis and may provide amino acids and energy for foreign polypeptide synthesis and secretion.

The length of time for the growth and the production phase will also impact yield and degradation. The length of these phases will vary depending on the host cells and polypeptide of interest being expressed. The optimal time of these phases can be determined empirically.

It is recognized that all of the above mentioned conditions which impact polypeptide yield and degradation may need to be varied depending on the scale of the culturing conditions (i.e., small scale, shake flask cultures or large scale fermentation). It is within skill in the art to determine the optimal expression conditions for the desired scale of culturing.

In preferred embodiments, conditions for the regulated expression of a polypeptide or interest using the PpSEC10 transcriptional regulatory element operably linked to a transcriptional initiation region will result in the polypeptide of interest comprising about 2% to 10%, about 10% to 25%, about 25%–40%, more preferably about 40% to 55%, about 55% to 70%, about 70% to 80%, and most preferably greater than 80% of the total cellular polypeptide produced by the host cell.

The secreted polypeptide of interest can be harvested by any conventional means and purified from media components by methods comprising, for example, chromatography, electrophoresis, dialysis, solvent-solvent extraction, and the like. The method of polypeptide purification will be based on the polypeptide of interest. In preferred embodiments the heterologous polypeptide of interest is IGF-1 or a variant or fragment thereof. Methods for the recombinant production and purification of IGF-1 in the yeast *Pichia pastoris* are described in U.S. Pat. Nos. 5,446,024; 5,231,178; 5,650,496 and International Publication No. WO 96/40776, herein incorporated by reference.

In a preferred embodiment, the heterologous nucleotide sequence of interest encodes an insulin-like growth factor I (IGF-I) polypeptide. IGF-I, a member of the somatomedin family that has 70 amino acid residues and a molecular mass of approximately 7.5 kDa. See Ringerknecht (1978) *J. Biol. Chem.* 253:2769 and *FEBS Lett.* 89:283. For a review of IGF-I, see Humbel (1990) *Eur. J. Biochem.* 190:445–462. The nucleotide sequence encoding IGF-I that is assembled as part of the DNA construct may be genomic, cDNA, or synthetic DNA. The genes encoding the native forms of IGF-I have been sequenced, and several variants are well known in the art.

Suitable variants can be IGF-I fragments, analogues, and derivatives. By "IGF-I fragment" is intended a polypeptide consisting of only a part of the intact IGF-I sequence and structure, and can be a C-terminal deletion or N-terminal deletion of IGF-I. By "analogues" is intended analogues of either IGF-I or an IGF-I fragment that comprise a native IGF-I sequence and structure having one or more amino acid substitutions, insertions, or deletions. Peptides having one or more peptoids (peptide mimics) are also encompassed by the term analogue (see International Publication No. WO 91/04282). By "derivatives" is intended any suitable modification of IGF-I, IGF-I fragments, or their respective analogues, such as glycosylation, phosphorylation, or other addition of foreign moieties, so long as the IGF-I activity is retained. Methods for making IGF-I fragments, analogues, and derivatives are available in the art. See generally U.S. Pat. Nos. 4,738,921, 5,158,875, and 5,077,276; International Publication Nos. WO 85/00831, WO 92/04363, WO 87/01038, and WO 89/05822; and European Patent Nos. EP 135094, EP 123228, and EP 128733; herein incorporated by reference. IGF-I variants will generally have at least 70%, at least 80%, at least about 90% to 95% or more, or about 95%, 96%, 97%, 98%, 99%, or more amino acid sequence identity to the amino acid sequence of the reference IGF-I molecule. A variant may differ by as few as 10, as few as 5, as few as 4, 3, 2, or even 1 amino acid residue.

The art provides substantial guidance regarding the preparation and use of such IGF-I variants, as discussed further below. A fragment of IGF-I will generally include at least 10 contiguous amino acid residues of the full-length molecule, preferably 15 contiguous amino acid residues of the full-length molecule, and most preferably 25 or more contiguous amino acid residues of full-length IGF-I. In preparing the IGF-I variants, one of skill in the art can readily determine which modifications to the native polypeptide nucleotide or amino acid sequence will result in a variant that retains the activity of the native IGF-I polypeptide. These will generally be conservative amino acid substitutions that preserve the charge of the substituted residue (e.g., aspartic acid for glutamic acid).

Methods for making IGF-1 fragments, analogues, and derivatives are available in the art. See generally U.S. Pat. Nos. 4,738,921, 5,158,875, and 5,077,276; International Publication Nos. WO 85/00831, WO 92/04363, WO 87/01038, and WO 89/05822; and European Patent Nos. EP 135094, EP 123228, and EP 128733; herein incorporated by reference.

Several IGF-I variants are known in the art and include those described in, for example, *Proc. Natl. Acad. Sci. USA* 83 (1986) 4904–4907; *Biochem. Biophys. Res. Commun.* 149 (1987) 398–404; *J. Biol. Chem.* 263 (1988) 6233–6239; *Biochem. Biophys. Res. Commun.* 165 (1989) 766–771; Forsbert et al. (1990) *Biochem. J.* 271:357–363; U.S. Pat. Nos. 4,876,242 and 5,077,276; and International Publication Nos. WO 87/01038 and WO 89/05822. Representative variants include one with a deletion of Glu-3 of the mature molecule, a variant with up to 5 amino acids truncated from the N-terminus, a variant with a truncation of the first 3 N-terminal amino acids (referred to as des(1–3)-IGF-I, des-IGF-I, tIGF-I, or brain IGF), and a variant including the first 17 amino acids of the B chain of human insulin in place of the first 16 amino acids of human IGF-I.

Nucleotide sequences encoding IGF-I are known in the art. The IGF-I coding sequence may be chemically synthesized, such as with the phosphoramidite procedure as described by Urea (1983) *Proc. Natl. Acad. Sci. USA* 80:7461, and according to the Dayhoff amino acid sequences. The human gene for IGF-I has been chemically synthesized as disclosed in Niwa et al. (1986) *Annals New York Acad. Sci.* 469:31–52 or Buell et al. (1985) *Nucleic Acids Res.* 13:1923–1938; herein incorporated by reference. Nucleotide sequences encoding IGF-I may also be obtained by transcription of messenger RNA corresponding to IGF-I into its complementary DNA and converting the latter into double-stranded cDNA. Alternatively, the nucleotide sequence encoding IGF-I may be directly obtained from a known vector comprising an IGF-I gene by using restriction enzyme digestion to remove the gene for subsequent insertion into the recombinant DNA construct of the present invention. Such vectors are known in the art, as, for example, the vectors disclosed in Niwa et al. (1986) *Annals New York Acad. Sci.* 469:31–52 and Buell et al. (1985) *Nucleic Acids Res.* 13:1923–1938. See also International Publication No. WO 97/12044, herein incorporated by reference.

The following examples are offered by way of illustration and not by way of limitation.

EXPERIMENTAL

Example 1

Iron Regulation of SEC10p Polypeptide Expression

The regulated expression of the SEC10p polypeptide by iron was determined by performing a shake flask experiment. Twenty ml of Pichia expression media (1× yeast nitrogen base (YNB): 1% casmino acids, 20 mg/L tryptophan, 20 mg/L histidine, 0.1 M sodium phosphate pH 6.0, and 2% glycerol) was inoculated with 0.1 ml of a stationary culture of *Pichia pastoris* strain SMD1163. Various amounts of Ferric Chloride ($FeCl_3$) were added to each culture with the final $FeCl_3$ concentration, ranging between 1 $\mu$M and 11 $\mu$M. The cultures were grown for 24 hours and the levels of SEC10p polypeptide under the various culturing conditions were analyzed by SDS gel electrophoresis.

The highest steady state levels of SEC10 polypeptide occurred in culturing media containing 1 $\mu$M to 1.75 $\mu$M $FeCl_3$. Moderate steady state levels of SEC10p occurred in culturing media containing between 2 to 3 $\mu$M $FeCl_3$ and low levels of SEC10p occurred in media containing 4 $\mu$M $FeCl_3$. SEC10p was not detected when $FeCl_3$ was added at concentrations between of 5 $\mu$M and 11 $\mu$M (data not shown). These results demonstrate that SEC10p polypeptide expression is regulated by Fe.

Example 2

Regulated Expression of a Heterologous Polpeptide Using the PpSEC10 Transcriptional Control Region To determine if the regulation of SEC10p expression by Fe was occurring at the transcriptional level, two reporter constructs utilizing the *P. pastoris* acid phosphatase (PHO1p) coding sequences were generated. The PHO1 encoded acid phosphate is normally secreted from *P. pastoris* (Payne et al. (1995) *Gene* 163:19–26) and is easily assayed.

The first construct, designated SECPho1, comprises the PpSEC10 transcriptional control element, operably linked to the PpSEC10 secretion leader, fused in frame with the nucleotide sequence encoding the *P. pastoris* acid phosphatase (Pho1p), followed by the PpSEC10 terminator sequence. The second reporter construction, designated Pho (wt), comprises the PpSEC10 transcriptional control element, operably linked to the secretion leader sequence of Pho1, fused in frame with the coding region of Pho1 and followed by the PpSEC10 terminator sequence. Each DNA constructs was inserted into a plasmid containing the ampicillin selectable marker.

The two reporter constructs were transformed into the SMD1163 *P. pastoris* strain. The transformed strains carrying either the Pho(wt) or the SECPho1 constructs were subsequently used in shake flask experiments. 20 mls of Pichia expression media was inoculated with 0.1 ml of saturated culture from either the Pho(wt), SECPho1, or untransformed SMD1163 strains. The cultures were grown in various concentrations of ferric chloride ($FeCl_3$). Following a 24-hour growth period the cultures were analyzed for acid phosphatase activity.

The total acid phosphatase activity secreted (absorbance at 420 nM) per optical density of the *P. pastoris* culture (OD 650) was determined as described by Kaiser et al. (1995) *Gene* 163: 16–26. Table 1 summarizes the effect of Fe concentration on the phosphatase activity in the culture media. Increasing the Fe concentration from 1 µM to 11 µM reduces the phosphatase activity in the cell culture by 117 fold. This reduction in phosphatase activity demonstrates the transcriptional control region of the PpSEC10 gene is regulated by Fe.

TABLE 1

Regulation of PpSEC10 transcriptional control region as measured by phosphatase activity

| Strain | FeCl$_3$ Concentration | Pho 1 Units/OD |
|---|---|---|
| SMD 1163 | 1 µM | 0.075 |
| SMD 1163 | 21 µM | −0.018 |
| Sec Pho 1 | 1 µM | 50.1 |
|  | 3 µM | 4.17 |
|  | 4 µM | 2.30 |
|  | 6 µM | 1.68 |
|  | 8 µM | 0.489 |
|  | 11 µM | 0.426 |
|  | 16 µM | 0.354 |
|  | 21 µM | 0.534 |
| Pho 1 (wt) | 3 µM | 3.26 |
|  | 6 µM | 1.32 |
|  | 11 µM | 0.789 |

Example 3
Mapping of the Transcriptional Regulatory Region of the PpSEC10 Promoter The Fe-responsive transcriptional regulatory region of the PpSEC10 promoter was mapped using the Pho(wt) reporter construction and the Acid Phosphatase Assay described in example 2. A series of reporter constructions were generated in which the size of the PpSEC10 promoter was reduced via a series of 5' end deletions. The 5' end deletions resulted in the Pho(wt) reporter being operably linked to PpSEC10 promoter sequences comprising 829 bp, 626 bp, 514 bp, 422 bp, and 337 bp. Each reporter construction was inserted into a plasmid containing an ampicillin selectable marker gene and transformed into the SMD1163 *P. pastoris* strain.

The transformed strains carrying SMD1163 strains transformed with the Pho(wt) constructs were subsequently used in shake flask experiments. 20 mls of Pichia expression media was inoculated with 0.1 ml of stationary culture of either Pho(wt) constructions containing varying lengths of the PpSEC10 promoter or untransformed SMD1163 strains. The cultures were grown in 2 µM ferric chloride (FeCl$_3$). Following a 17-hour and a 24-hour growth period the cultures were analyzed for acid phosphatase activity using the methods described in example 2. The results are summarized in Table 2. The 829 bp, 626 bp, 514 bp, and 422 bp PpSEC10 promoters activate transcription of the Pho1 reporter under low Fe conditions. The 337 bp promoter does not activate transcription of the Pho1 reporter under low Fe conditions. These results indicate that the Fe-responsive element within the PpSEC10 transcriptional control region is located between about nucleotide 422 and about nucleotide 337 of the PpSEC10 promoter. The region of the PpSEC10 promoter comprising nucleotides 422 to 337 relative to the 3' end of the promoter is shown in SEQ ID NO:6.

The DNA constructs described above containing the 5' deletions of the PpSEC10 promoter further comprised a 6 nucleotide linker (GAATTC) between the PpSEC10 promoter and the ATG of the Pho reporter sequence. Consequently, the actual length of the PpSEC10 promoter is 6 nucleotides shorter than the constructions nomenclature indicates. The results from these constructions are presented in Table 2. The results indicate that the Fe-responsive element within the PpSEC10 transcriptional control region is located between about nucleotide 416 and about nucleotide 330 relative to the 3' end of the PpSEC10 promoter. This region of the promoter is set forth in SEQ ID NO:1.

TABLE 2

Mapping of the Transcriptional Regulatory Region of the PpSEC10 Promoter as measured by phosphatase activity.

|  | Pho 1 Units/OD (A$_{420}$/OD) | |
|---|---|---|
| Construction | 17 hrs | 25 hrs |
| Negative control | 0.016 | 0.006 |
| 829 bp promoter/Pho 1 | 0.032 | 0.073 |
| 626 bp promoter/Pho 1 | 0.034 | 0.081 |
| 514 bp promoter/Pho 1 | 0.025 | 0.072 |
| 422 bp promoter/Pho 1 | 0.031 | 0.072 |
| 337 bp promoter/Pho 1 | 0.014 | 0.005 |

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

That which is claimed is:

1. A method of expressing a nucleotide sequence of interest said method comprising: stably introducing into a yeast host cell at least one DNA construct comprising an Fe-responsive transcriptional regulatory region, operably linked to a heterologous transcriptional initiation region operably linked to the nucleotide sequence of interest, and culturing said yeast host cell in media, wherein said Fe-responsive transcriptional regulatory region is a nucleotide sequence having at least 70% sequence identity to the sequence set forth in SEQ ID NO:1, wherein the sequence identity to SEQ ID NO:1 is determined using the Smith-Waterman homology search algorithm using a gap open penalty of 25 and a gap extension penalty of 5.

2. The method of claim 1, wherein the expression of the nucleotide sequence of interest is regulated by modulating the Fe concentration of the media.

3. The method of claim 1, wherein the Fe-responsive transcriptional regulatory region comprises the nucleotide sequence set forth in SEQ ID NO:1.

4. The method of claim 1, wherein said yeast host cell is a member of the genus selected from the group consisting of Pichia, Saccharomyces, and Kluyveramyces.

5. The method of claim 4, wherein said yeast host cell is selected from the group consisting of *Pichia pastoris, Saccharomyces cerevisiae,* and *Kluyveromyces lactis.*

6. The method of claim 1, wherein said yeast host cell is from Pichia.

7. The method of claim 6, wherein said yeast host cell is from *Pichia pastoris.*

8. The method of claim 2, wherein said media contains a sufficient concentration of Fe to repress the expression of said nucleotide sequence of interest.

9. The method of claim 8, wherein said media contains about 5 μM to 20 μM Fe.

10. The method of claim 2, wherein said media contains a sufficient concentration of Fe to activate the expression of said nucleotide sequence of interest.

11. The method of claim 10, wherein said media contains less than 1 μM to about 2 μM Fe.

12. The method of claim 1, wherein said nucleotide sequence of interest encodes a polypeptide.

13. The method of claim 12, further comprising the isolation of the polypeptide.

14. The method of claim 12, wherein said nucleotide sequence of interest encodes IGF-1, a biologically active fragment of IGF-1 comprising at least 10 contiguous amino acids of IGF-1, or abiologically active variant or IGF-1 comprising at least 70% sequence identity to the amino acid sequence of IGF-1, wherein the sequence identity to IGF-1 is determined using the Smith-Waterman homology search algorithm using an affine 6 gap search with a gap open penalty of 12 and a gap extension penalty of 2 and the BLOSUM matrix 62.

15. The method of claim 1, wherein said DNA construct further comprises a nucleotide sequence encoding a secretion leader.

16. A method to regulate expression of a nucleotide sequence of interest said method comprising: stably introducing into a yeast host cell at least one DNA construct comprising an Fe-responsive transcriptional regulatory region, operably linked to a transcriptional initiation region operably linked to a nucleolide sequence of interest, and culturing said yeast host cell in media, wherein the expression of the nucleotide sequence of interest is regulated by modulating the Fe concentration of the media, said Fe-responsive transcriptional regulatory region is a nucleotide sequence having at least 70% sequence identity to the sequence set forth in SEQ ID NO:1, wherein the sequence identity to SEQ ID NO:1 is determined using the Smith-Waterman homology search algorithm using a gap open penalty of 25 and a gap extension penalty of 5.

17. The method of claim 16, wherein the modulation of the Fe concentration in the media comprises:
   culturing said yeast host cell in media, wherein the Fe concentration is sufficient to repress the expression of the nucleotide sequence of interest; and,
   reducing the concentration of Fe in the media to induce expression of the nucleotide sequence of interest.

18. The method of claim 16, wherein the Fe-responsive transcriptional regulatory region comprises the nucleotide sequence set forth in SEQ ID NO:1.

19. The method of claim 16, wherein said transcriptional initiation region is homologous to the Fe-responsive transcriptional regulatory region.

20. The method of claim 19, wherein the transcriptional initiation region is from PpSEC10.

21. The method of claim 16, wherein said transcriptional initiation region is heterologous to the Fe-responsive transcriptional regulatory region.

22. A DNA construct comprising an Fe-responsive transcriptional regulatory region, operably linked to a heterologous transcriptional initiation region operably linked to a nucleotide sequence of interest, wherein said Fe-responsive transcriptional regulatory region is a nucleotide sequence having at least 70% sequence identity to the sequence set forth in SEQ ID NO:1, wherein the sequence identity to SEQ ID NO:1 is determined using the Smith-Waterman homology search algorithm using a gap open penalty of 25 and a gap extension penalty of 5.

23. An expression vector comprising the DNA construct of claim 22.

24. The DNA construct of claim 22, wherein said nucleotide sequence of interest encodes IGF-1, a biologically active fragment of IGF-1 comprising at least 10 contiguous amino acids of IGF-1, or a biologically active variant of IGF-1 comprising at least 70% sequence identity to the amino acid sequence of IGF-1, wherein the sequence identity to IGF-1 is determined using the Smith-Waterman homology search algorithm using an affine 6 gap search with a gap open penalty of 12 and a gap extension penalty of 2 and the BLOSUM matrix 62.

25. A method of expressing a nucleotide sequence of interest said method comprises: stably introducing into a yeast host cell at least one DNA construct comprising an Fe-responsive transcriptional regulatory region operably linked to a transcriptional initiation region operably linked to said nucleotide sequence of interest, and culturing said yeast host cell in media comprising less than 1 $\mu$M Fe, wherein said Fe-responsive transcriptional regulatory region is a nucleotide sequence having at least 70% sequence identity to the sequence set forth in SEQ ID NO:1, wherein the sequence identity of SEQ ID NO:1 is determined using the Smith-Waterman homology search algorithm using a gap open penalty of 25 and a gap extension penalty of 5.

26. The method of claim 25, wherein said transcriptional initiation region is from PpSEC10.

27. The method of claim 25, wherein said transcriptional initiation region is heterologous to the Fe-responsive transcriptional regulatory region.

28. A method of expressing a nucleotide sequence of interest, said a method comprises: growing a yeast host cell having at least one transcriptional control region comprising a Fe-responsive transcriptional regulatory region, operably linked to said nucleotide sequence of interest, and culturing said yeast host cell in media comprising less than 1 $\mu$M Fe, wherein said Fe-responsive transcriptional regulatory region is a nucleotide sequence having at least 70% sequence identity to the sequence set forth in SEQ ID NO:1, wherein the sequence identity to SEQ ID NO:1 is determined using the Smith-Waterman homology search algorithm using a gap open penalty of 25 and a gap extention penalty of 5.

29. A method of regulating the expression of a nucleotide sequence of interest, said method comprises: growing a yeast host cell having at least one transcriptional control region comprising a Fe-responsive transcriptional regulatory region operably linked to said nucleotide sequence of interest and culturing said yeast host cell in media, wherein the Fe concentration of the culture media is modulated, said Fe-responsive transcriptional regulatory region is a nucleotide sequence having at least 70% sequence identity to the sequence set forth in SEQ ID NO:1, wherein the sequence identity to SEQ ID NO:1 is determined using the Smith-Waterman homology search algorithm using a gap open penalty of 25 and a gap extension penalty of 5.

30. The method of claim 28, wherein the nucleic acid sequence of interest is not SEQ ID NO:3.

31. The method of claim 29, wherein the nucleic acid sequence of interest is not SEQ ID NO:3.

32. The method of claim 1, wherein said Fe-responsive transcriptional regulatory region is a nucleotide sequence having at least 90% sequence identity to the sequence set forth in SEQ ID NO:1, wherein the sequence identity to SEQ ID NO:1 is determined using the Smith-Waterman homology search algorithm using a gap open penalty of 25 and a gap extension penalty of 5.

33. The method of claim 32, wherein said Fe-responsive transcriptional regulatory region is a nucleotide sequence having at least 95% sequence identity to the sequence set forth in SEQ ID NO:1, wherein the sequence identity to SEQ ID NO:1 is determined using the Smith-Waterman homology search algorithm using a gap open penalty of 25 and a gap extension penalty of 5.

34. A method of expressing a nucleotide sequence of interest said method comprising: stably introducing into a yeast host cell at least one DNA construct comprising an Fe-responsive transcriptional regulatory region, operably linked to a heterologous transcriptional initiation region operably linked to the nucleotide sequence of interest, and culturing said yeast host cell in media, wherein said Fe-responsive transcriptional regulatory region is selected from the group consisting of:
  a) a nucleotide sequence comprising at least 15 contiguous nucleotides of the sequence set forth in SEQ ID NO:1; and,
  b) a nucleotide sequence that hybridizes under stringent conditions to the complement of a nucleotide sequence set forth in SEQ ID NO:1.

35. The method of claim 16, wherein said Fe-responsive transcriptional regulatory region is a nucleotide sequence having at least 90% sequence identity to the sequence set forth in SEQ ID NO:1, wherein the sequence identity to SEQ ID NO:1 is determined using the Smith-Waterman homology search algorithm using a gap open penalty of 25 and a gap extension penalty of 5.

36. The method of claim 35, wherein said Fe-responsive transcriptional regulatory region is a nucleotide sequence having at least 95% sequence identity to the sequence set forth in SEQ ID NO:1, wherein the sequence identity to SEQ ID NO:1 is determined using the Smith-Waterman homology search algorithm using a gap open penalty of 25 and a gap extension penalty of 5.

37. A method to regulate expression of a nucleotide sequence of interest said method comprising: stably introducing into a yeast host cell at least one DNA construct comprising an Fe-responsive transcriptional regulatory region, operably linked to a transcriptional initiation region operably linked to a nucleotide sequence of interest, and culturing said yeast host cell in media, wherein the expression of the nucleotide sequence of interest is regulated by modulating the Fe concentration of the media, said Fe-responsive transcription regulatory region being selected from the group consisting of:
  a) a nucleotide sequence comprising at least 15 contiguous nucleotides of the sequence set forth in SEQ ID NO:1; and,
  b) a nucleotide sequence that hybridizes under stringent conditions to the complement of the nucleotide sequence comprising the sequence set forth in SEQ ID NO:1.

38. The DNA construct of claim 22, wherein said Fe-responsive transcriptional regulatory region is a nucleotide sequence having at least 90% sequence identity to the sequence set forth in SEQ ID NO:1, wherein the sequence identity to SEQ ID NO:1 is determined using the Smith-Waterman homology search algorithm using a gap open penalty of 25 and a gap extension penalty of 5.

39. The DNA construct of claim 38, wherein said Fe-responsive transcriptional regulatory region is a nucleotide sequence having at least 95% sequence identity to the sequence set forth in SEQ ID NO:1, wherein the sequence identity to SEQ ID NO:1 is determined using the Smith-Waterman homology search algorithm using a gap open penalty of 25 and a gap extension penalty of 5.

40. The DNA construct of claim 39, wherein said Fe-responsive transcriptional regulatory region is the nucleotide sequence set forth in SEQ ID NO:1.

41. A DNA construct comprising an Fe-responsive transcriptional regulatory region, operably linked to a heterologous transcriptional initiation region operably linked to a nucleotide sequence of interest, wherein said Fe-responsive transcriptional regulatory region is selected from the group consisting of:
   a) a nucleotide sequence that hybridizes under stringent conditions to the complement of a nucleotide sequence comprising at least 15 contiguous nucleotides of the sequence set forth in SEQ ID NO:1; and,
   b) a nucleotide sequence that hybridizes under stringent conditions to the complement of a nucleotide sequence having at least 70% sequence identity to the sequence set forth in SEQ ID NO:1, wherein the sequence identity to SEQ ID NO:1 is determined using the Smith-Waterman homology search algorithm using a gap open penalty of 25 and a gap extension penalty of 5.

42. The DNA construct of claim 41, wherein Fe-responsive transcriptional regulatory region is selected from the group consisting of:
   a) a nucleotide sequence comprising at least 15 contiguous nucleotides of the sequence set forth in SEQ ID NO:1; and,
   b) a nucleotide sequence that hybridizes under stringent conditions to the complement of a nucleotide sequence comprising the sequence set forth in SEQ ID NO:1.

43. The method of claim 25, wherein said Fe-responsive transcriptional regulatory region is a nucleotide sequence having at least 90% sequence identity to the sequence set forth in SEQ ID NO:1, wherein the sequence identity to SEQ ID NO:1 is determined using the Smith-Waterman homology search algorithm using a gap open penalty of 25 and a gap extension penalty of 5.

44. The method of claim 43, wherein said Fe-responsive transcriptional regulatory region is a nucleotide sequence having at least 95% sequence identity to the sequence set forth in SEQ ID NO:1, wherein the sequence identity to SEQ ID NO:1 is determined using the Smith-Waterman homology search algorithm using a gap open penalty of 25 and a gap extension penalty of 5.

45. The method of claim 44, wherein said Fe-responsive transcriptional regulatory region is a nucleotide sequence is the sequence set forth in SEQ ID NO:1.

46. A method of expressing a nucleotide sequence of interest said method comprises: stably introducing into a yeast host cell at least one DNA construct comprising a Fe-responsive transcriptional regulatory region operably linked to a transcriptional initiation region operably linked to said nucleotide sequence of interest, and culturing said yeast host cell in media comprising less than 1 $\mu$M Fe, wherein said Fe-responsive transcriptional regulatory region is selected from the group consisting of:
   a) a nucleotide sequence that hybridizes under stringent conditions to the complement of a nucleotide sequence comprising the sequence set forth in SEQ ID NO:1; and,
   b) a nucleotide sequence comprising at least 15 contiguous nucleotides of the sequence set forth in SEQ ID NO:1.

47. The method of claim 28, wherein said Fe-responsive transcriptional regulatory region is a nucleotide sequence having at least 90% sequence identity to the sequence set forth in SEQ ID NO:1, wherein the sequence identity to SEQ ID NO:1 is determined using the Smith-Waterman homology search algorithm using a gap open penalty of 25 and a gap extension penalty of 5.

48. The method of claim 47, wherein said Fe-responsive transcriptional regulatory region is a nucleotide sequence having at least 95% sequence identity to the sequence set forth in SEQ ID NO:1, wherein the sequence identity to SEQ ID NO:1 is determined using the Smith-Waterman homology search algorithm using a gap open penalty of 25 and a gap extension penalty of 5.

49. The method of claim 48, wherein said Fe-responsive transcriptional regulatory region is a nucleotide sequence comprising the sequence set forth in SEQ ID NO:1.

50. A method of expressing a nucleotide sequence of interest, said method comprises: growing a yeast host cell having at least one transcription control region comprising a Fe-responsive transcriptional regulatory region operably linked to said nucleotide sequence of interest, and culturing said yeast host cell in media comprising less than 1 $\mu$M Fe, wherein said Fe-responsive transcriptional regulatory region is selected from the group consisting of:
   a) a nucleotide sequence that hybridizes under stringent conditions to the complement of a nucleotide sequence comprising the sequences set forth in SEQ ID NO:1; and,
   b) a nucleotide sequence comprising at least 15 contiguous nucleotides of the sequence set forth in SEQ ID NO:1.

51. The method of claim 29, wherein said Fe-responsive transcriptional regulatory region is a nucleotide sequence having at least 90% sequence identity to the sequence set forth in SEQ ID NO:1, wherein the sequence identity to SEQ ID NO:1 is determined using the Smith-Waterman homology search algorithm using a gap open penalty of 25 and a gap extension penalty of 5.

52. The DNA construct of claim 51, wherein said Fe-responsive transcriptional regulatory region is a nucleotide sequence having at least 95% sequence identity to the sequence set forth in SEQ ID NO:1, wherein the sequence identity of SEQ ID NO:1 is determined using the Smith-Waterman homology search algorithm using a gap open penalty of 25 and a gap extension penalty of 5.

53. The method of claim 52, wherein said Fe-responsive transcriptional regulatory region is a nucleotide sequence comprising the sequence set forth in SEQ ID NO:1.

54. A method of regulating the expression of a nucleotide sequence of interest, said method comprises: growing a yeast host cell having at least one transcriptional control region comprising a Fe-responsive transcriptional regulatory region operably linked to said nucleotide sequence of interest and culturing said yeast host cell in media, wherein the Fe concentration of the culture media is modulated, said Fe-responsive transcriptional regulatory region being selected from the group consisting of:
   a) a nucleotide sequence that hybridizes under stringent conditions to the complement of a nucleotide sequence comprising the sequence set forth in SEQ ID NO:1; and,
   b) a nucleotide sequence comprising at least 15 contiguous nucleotides of the sequence set forth in SEQ ID NO:1.

* * * * *

UNITED STATES PATENT AND TRADEMARK OFFICE
CERTIFICATE OF CORRECTION

PATENT NO. : 6,605,450 B1
DATED : August 12, 2003
INVENTOR(S) : Bishop et al.

It is certified that error appears in the above-identified patent and that said Letters Patent is hereby corrected as shown below:

<u>Column 29,</u>
Line 43, "Kluyveramyces" should read -- Kluyveromyces --.

<u>Column 30,</u>
Line 21, "abiologically" should read -- a biologically --; "or" (second occurance) should read -- of --.

<u>Column 33,</u>
Line 26, after "wherein" insert -- said --;

<u>Column 34,</u>
Line 28, "sequences" should read -- sequence --;
Line 40, "DNA construct" should read -- method --;
Line 44, "of" should read -- to --.

Signed and Sealed this

Sixteenth Day of March, 2004

JON W. DUDAS
*Acting Director of the United States Patent and Trademark Office*

SEQUENCE LISTING

<160> NUMBER OF SEQ ID NOS: 7

<210> SEQ ID NO 1
<211> LENGTH: 87
<212> TYPE: DNA
<213> ORGANISM: Pichia pastoris

<400> SEQUENCE: 1
tgttagctgc attttcatga tacggataga agtcgttcaa tgacccgagt tatcaaaggg      60
atagattgat tgcaattgga ctcgtgc                                          87

<210> SEQ ID NO 2
<211> LENGTH: 1108
<212> TYPE: DNA
<213> ORGANISM: Pichia pastoris
<220> FEATURE:
<221> NAME/KEY: misc_feature
<222> LOCATION: (0)...(0)
<223> OTHER INFORMATION: transcriptional control region of PpSec10

<400> SEQUENCE: 2

```
gtgatctttg gcttgatcgc agcaggttat tgacagttat gccaggaact tagagcataa      60
aactttgaac tgttctgcaa tatcagattg gaccaaatac tcactaccct aattctcata     120
tcttttcgat aagaggttgc ttcaattagt tggctggcca caatctcagg tgctctgcca     180
ttatgaggtc tgggtaagtc cagcttggaa agcaatttcg caaatcgcga tgtgtaaatc     240
taccccctcc gatacaaata caactttagg ggggtatcat attagaatgc attatacgag     300
ccaggggtaa acctattcag aggattcaag ccgaggatca attcgcaaca aaagaattga     360
caatgctgta caataatccg tagtaaccta agactggtta catgtacgac ctcccgcccc     420
ccacgacccc ccacttataa tttcaaagtt tcagggagca caatatagag ggctttgtca     480
agcagctgac tagtaaaggt aaagctatgg aatatatgtg aatggtgact tgacaccgat     540
gcagaatacc cactggaaag tcgggtttta acaggataga tgaactgtga tcctgtgcga     600
ccaaagccta gatattgtaa gcacgagaat ctatatgact tgaaggttgt attgctctgt     660
gaacttaact ttcctgttct tcaattttca aatgttagct gcattttcat gatacggata     720
gaagtcgttc aatgacccga gttatcaaag ggatagattg attgcaattg gactcgtgca     780
tgcacatttc gcttcgttac ggcacccgat acgaccacaa gagtgtagtc aagtgttatg     840
gtaggtggaa atttcggatt catcgctaat caacggggat agcgtatttt tagtgaactt     900
gaccttttt ttccgaacaa aataagcccc ccttcagct aaaagagggt agtgttgaca     960
tttttaccat gcagggggat gcaaggagac tgctgagcat gagttactgc cttctaggtt    1020
ttgacagaag tttatataac gtgccattca tatcgtttta acgtcagaac tatctcctct    1080
tctttgattc ttcaacttaa cactcaaa                                       1108
```

<210> SEQ ID NO 3
<211> LENGTH: 459
<212> TYPE: DNA
<213> ORGANISM: Pichia pastoris
<220> FEATURE:
<221> NAME/KEY: CDS
<222> LOCATION: (1)...(459)
<223> OTHER INFORMATION: SEC10P
<221> NAME/KEY: mat_peptide
<222> LOCATION: (156)...(300)
<221> NAME/KEY: sig_peptide
<222> LOCATION: (1)...(156)

<400> SEQUENCE: 3

```
atg cta ttc aac aaa ttt gcc gca acc cta cta tct gct att gct gca       48
Met Leu Phe Asn Lys Phe Ala Ala Thr Leu Leu Ser Ala Ile Ala Ala
    -50                 -45                 -40 gta aat gca att tct ttg cct tcc att gaa cag gca cgt gaa cat gta       96
Val Asn Ala Ile Ser Leu Pro Ser Ile Glu Gln Ala Arg Glu His Val
        -35                 -30                 -25 gcc aga ggt ctt gtt cct cag gcc ttt gct gac gct ttg gat cct gct      144
Ala Arg Gly Leu Val Pro Gln Ala Phe Ala Asp Ala Leu Asp Pro Ala
-20                 -15                 -10                  -5 ctt gaa aag aga gct gat tac atg tgt cac atg gct tgt ggt tta gcc      192
```

```
                    Leu Glu Lys Arg Ala Asp Tyr Met Cys His Met Ala Cys Gly Leu Ala
                                  1               5                  10 atc tac ggt gcc tgg gag tgt ggt ccc gag gca ggt cct ttc gac tca                 240
Ile Tyr Gly Ala Trp Glu Cys Gly Pro Glu Ala Gly Pro Phe Asp Ser
         15                  20                  25 gaa tgt cta tgt gcc act gat tcc tcc ttt tcg caa caa att gca gct                 288
Glu Cys Leu Cys Ala Thr Asp Ser Ser Phe Ser Gln Gln Ile Ala Ala
 30                  35                  40 tgt aac gat tgt gga tgg tgt ctt tac cag tct tac tat ggt tac cta                 336
Cys Asn Asp Cys Gly Trp Cys Leu Tyr Gln Ser Tyr Tyr Gly Tyr Leu
 45                  50                  55                  60 gct ggt cct ttg gac act tgc ggt ttg cca att act cca act ggt acc                 384
Ala Gly Pro Leu Asp Thr Cys Gly Leu Pro Ile Thr Pro Thr Gly Thr
                 65                  70                  75 caa tgt gct gag aca gct aca acg ttg acc cca act ata ggt cct ttc                 432
Gln Cys Ala Glu Thr Ala Thr Thr Leu Thr Pro Thr Ile Gly Pro Phe
             80                  85                  90 caa acc tat aca ccc act agt gtt taa                                             459
Gln Thr Tyr Thr Pro Thr Ser Val *
         95                 100

<210> SEQ ID NO 4
<211> LENGTH: 152
<212> TYPE: PRT
<213> ORGANISM: Pichia pastoris
<220> FEATURE:
<221> NAME/KEY: SIGNAL
<222> LOCATION: (1)...(52)

<400> SEQUENCE: 4

Met Leu Phe Asn Lys Phe Ala Ala Thr Leu Leu Ser Ala Ile Ala Ala
         -50                 -45                 -40

Val Asn Ala Ile Ser Leu Pro Ser Ile Glu Gln Ala Arg Glu His Val
         -35                 -30                 -25

Ala Arg Gly Leu Val Pro Gln Ala Phe Ala Asp Ala Leu Asp Pro Ala
 -20                 -15                 -10                  -5

Leu Glu Lys Arg Ala Asp Tyr Met Cys His Met Ala Cys Gly Leu Ala
              1                   5                  10

Ile Tyr Gly Ala Trp Glu Cys Gly Pro Glu Ala Gly Pro Phe Asp Ser
         15                  20                  25

Glu Cys Leu Cys Ala Thr Asp Ser Ser Phe Ser Gln Gln Ile Ala Ala
 30                  35                  40

Cys Asn Asp Cys Gly Trp Cys Leu Tyr Gln Ser Tyr Tyr Gly Tyr Leu
 45                  50                  55                  60

Ala Gly Pro Leu Asp Thr Cys Gly Leu Pro Ile Thr Pro Thr Gly Thr
                 65                  70                  75

Gln Cys Ala Glu Thr Ala Thr Thr Leu Thr Pro Thr Ile Gly Pro Phe
             80                  85                  90

Gln Thr Tyr Thr Pro Thr Ser Val
         95                 100

<210> SEQ ID NO 5
<211> LENGTH: 1021
<212> TYPE: DNA
<213> ORGANISM: Pichia pastoris
<220> FEATURE:
<221> NAME/KEY: misc_feature
<222> LOCATION: (0)...(0)
<223> OTHER INFORMATION: Transcriptional control region of PpSEC10
      with the Fe regulatory region of SEQ ID NO:1 removed
```

-continued

```
<400> SEQUENCE: 5
gtgatctttg gcttgatcgc agcaggttat tgacagttat gccaggaact tagagcataa      60
aactttgaac tgttctgcaa tatcagattg gaccaaatac tcactaccct aattctcata     120
tcttttcgat aagaggttgc ttcaattagt tggctggcca caatctcagg tgctctgcca     180
ttatgaggtc tgggtaagtc cagcttggaa agcaatttcg caaatcgcga tgtgtaaatc     240
taccccctcc gatacaaata caactttagg ggggtatcat attagaatgc attatacgag     300 ccagggtaa  acctattcag aggattcaag ccgaggatca attcgcaaca aaagaattga     360
caatgctgta caataatccg tagtaaccta agactggtta catgtacgac ctcccgcccc     420
ccacgacccc ccactataa  tttcaaagtt tcagggagca caatatagag ggctttgtca     480
agcagctgac tagtaaaggt aaagctatgg aatatatgtg aatggtgact tgacaccgat     540
gcagaatacc cactgaaaag tcgggtttta acaggataga tgaactgtga tcctgtgcga     600
ccaaagccta gatattgtaa gcacgagaat ctatatgact tgaaggttgt attgctctgt     660
gaacttaact ttcctgttct tcaattttca aaatgcacat ttcgcttcgt tacggcaccc     720
gatacgacca caagagtgta gtcaagtgtt atggtaggtg gaaatttcgg attcatcgct     780
aatcaacggg gatagcgtat ttttagtgaa cttgacccct tttttccgaa caaaataagc     840
cctcccttca gctaaaagag ggtagtgttg acattttttac catgcaggg  gatgcaagga    900 gactgctgag catgagttac tgccttctag gttttgacag aagtttatat aacgtgccat     960
tcatatcgtt ttaacgtcag aactatctcc tcttctttga ttcttcaact taacactcaa    1020
a                                                                    1021

<210> SEQ ID NO 6
<211> LENGTH: 85
<212> TYPE: DNA
<213> ORGANISM: Pichia pastoris

<400> SEQUENCE: 6
ttcaaatgtt agctgcattt tcatgatacg gatagaagtc gttcaatgac ccgagttatc      60
aaagggatag attgattgca attgg                                           85

<210> SEQ ID NO 7
<211> LENGTH: 1023
<212> TYPE: DNA
<213> ORGANISM: Pichia pastoris
<220> FEATURE:
<221> NAME/KEY: misc_feature
<222> LOCATION: (1)...(1022)
<223> OTHER INFORMATION: Transcriptional control region of PpSEC10 with
      the Fe regulatory region of SEQ ID NO:6 removed

<400> SEQUENCE: 7
gtgatctttg gcttgatcgc agcaggttat tgacagttat gccaggaact tagagcataa      60
aactttgaac tgttctgcaa tatcagattg gaccaaatac tcactaccct aattctcata     120
tcttttcgat aagaggttgc ttcaattagt tggctggcca caatctcagg tgctctgcca     180
ttatgaggtc tgggtaagtc cagcttggaa agcaatttcg caaatcgcga tgtgtaaatc     240
taccccctcc gatacaaata caactttagg ggggtatcat attagaatgc attatacgag     300 ccagggtaa  acctattcag aggattcaag ccgaggatca attcgcaaca aaagaattga     360
caatgctgta caataatccg tagtaaccta agactggtta catgtacgac ctcccgcccc     420
ccacgacccc ccactataa  tttcaaagtt tcagggagca caatatagag ggctttgtca     480
```

-continued

```
agcagctgac tagtaaaggt aaagctatgg aatatatgtg aatggtgact tgacaccgat      540
gcagaatacc cactggaaag tcgggtttta acaggataga tgaactgtga tcctgtgcga      600
ccaaagccta gatattgtaa gcacgagaat ctatatgact tgaaggttgt attgctctgt      660
gaacttaact ttcctgttct tcaattactc gtgcatgcac atttcgcttc gttacggcac      720
ccgatacgac cacaagagtg tagtcaagtg ttatggtagg tggaaatttc ggattcatcg      780
ctaatcaacg gggatagcgt atttttagtg aacttgaccc tttttttccg aacaaaataa      840
gccctccctt cagctaaaag agggtagtgt tgacatttt accatgcagg gggatgcaag       900
gagactgctg agcatgagtt actgccttct aggttttgac agaagtttat ataacgtgcc      960
attcatatcg ttttaacgtc agaactatct cctcttcttt gattcttcaa cttaacactc     1020
aaa                                                                   1023
```